(12) United States Patent
Liu (10) Patent No.: US 10,506,834 B2
(45) Date of Patent: *Dec. 17, 2019

(54) ELECTRONIC CIGARETTE AND ATOMIZER DEVICE THEREOF

(71) Applicant: SHENZHEN SMOORE TECHNOLOGY LIMITED, Shenzhen (CN)

(72) Inventor: Pingkun Liu, Shenzhen (CN)

(73) Assignee: SHENZHEN SMOORE TECHNOLOGY LIMITED, Shenzhen (CN)

(*) Notice: Subject to any disclaimer, the term of this patent is extended or adjusted under 35 U.S.C. 154(b) by 0 days.

This patent is subject to a terminal disclaimer.

(21) Appl. No.: 16/529,826

(22) Filed: Aug. 2, 2019

(65) Prior Publication Data

US 2019/0350268 A1 Nov. 21, 2019

Related U.S. Application Data

(63) Continuation of application No. 16/396,792, filed on Apr. 29, 2019, which is a continuation of application No. 15/551,606, filed as application No. PCT/CN2015/077448 on Apr. 24, 2015, now Pat. No. 10,306,929.

(51) Int. Cl.
| | |
|---|---|
| *A24F 13/00* | (2006.01) |
| *A24F 47/00* | (2006.01) |
| *A61M 11/04* | (2006.01) |
| *A61M 15/06* | (2006.01) |
| *F16K 3/04* | (2006.01) |

(52) U.S. Cl.
CPC ............ *A24F 47/008* (2013.01); *A24F 47/00* (2013.01); *A61M 11/042* (2014.02); *A61M 15/06* (2013.01); *F16K 3/04* (2013.01)

(58) Field of Classification Search
CPC ....................................................... A24F 47/00
USPC ................................................. 131/328–329
See application file for complete search history.

(56) References Cited

U.S. PATENT DOCUMENTS

| | | | |
|---|---|---|---|
| 6,170,490 B1* | 1/2001 | Barrow | A24F 19/0064 131/235.1 |
| 10,306,929 B2* | 6/2019 | Liu | A24F 47/00 |
| 2008/0093394 A1* | 4/2008 | Peterson | B65D 47/265 222/480 |

* cited by examiner

*Primary Examiner* — Phuong K Dinh
(74) *Attorney, Agent, or Firm* — Hemisphere Law, PLLC; Zhigang Ma (57) ABSTRACT

An electronic cigarette and an atomizer device thereof are provided. The atomizer device includes a housing, a liquid reservoir chamber (115) formed in the housing, and a adjusting valve (13) engaging with the housing; a liquid injection channel (1131) is defined in the housing for injecting liquid solution into the liquid reservoir chamber (115); a first opening (1311) corresponding to the liquid injection channel (1131) is defined in the adjusting valve (13); the adjusting valve (13) is movable between a first position and a second position across a surface of the housing; when the adjusting valve is in the first position, the first opening (1311) communicates with the liquid injection channel (1131) to open the liquid injection channel (1131), and when the adjusting valve (13) is in the second position, the first opening (1311) misaligns with the liquid injection channel (1131) to close the liquid injection channel (1131).

20 Claims, 11 Drawing Sheets

ELECTRONIC CIGARETTE AND ATOMIZER DEVICE THEREOF

TECHNICAL FIELD

The present disclosure relates to substitutes for cigarettes, and more particularly, to an electronic cigarette and an atomizer device thereof.

BACKGROUND

At present, for an electronic cigarette which can be repeatedly used, after liquid solution is used up, new liquid solution can be injected into a cartridge of the electronic cigarette, thus, the electronic cigarette can be continuously used. However, a suction nozzle of the electronic cigarette needs to be removed for injecting the liquid solution into the cartridge, which is troublesome. In addition, the suction nozzle removed from the electronic cigarette may easily drop off to get dirty or get lost, which is inconvenient.

SUMMARY OF THE DISCLOSURE

An improved electronic cigarette and an atomizer device thereof are improved in the present disclosure.

The atomizer device provided in the present disclosure includes a housing, a liquid reservoir chamber formed in the housing, and an adjusting valve engaging with the housing; a liquid injection channel is defined in the housing for injecting liquid solution into the liquid reservoir chamber; a first opening corresponding to the liquid injection channel is defined in the adjusting valve; the adjusting valve is movable between a first position and a second position across a surface of the housing; when the adjusting valve is in the first position, the first opening communicates with the liquid injection channel to open the liquid injection channel, and when the adjusting valve is in the second position, the first opening misaligns with the liquid injection channel to close the liquid injection channel.

Preferably, the housing includes an air flowing pipe, a cartridge sleeved on the air flowing pipe, and a sealing unit arranged on one end of the cartridge corresponding to the air flowing pipe; the liquid reservoir chamber is formed between the cartridge and the air flowing pipe; and the sealing unit seals one end of the liquid reservoir chamber, and the liquid injection channel is defined on the sealing unit.

Preferably, the sealing unit includes an annular sealing cover correspondingly engaging with the adjusting valve, and a second opening of the liquid injection channel is defined in the sealing cover; and the adjusting valve includes an annular adjusting cover rotatably contacting the sealing cover.

Preferably, a rotating ring is arranged on an outer ring of the adjusting cover for rotating the adjusting cover, and an outer wall of the rotating ring is provided with anti-skid designs.

Preferably, a sealing ring protrudes from one side of the sealing cover corresponding to the adjusting cover, and the sealing ring forms an enclosed structure around the second opening.

Preferably, the sealing unit includes a fastening member and a sealing plug; the fastening member includes an annular plate, a first sleeving portion arranged on an inner ring of the plate, and a second sleeving portion arranged on an outer ring of the plate; the first sleeving portion and the second sleeving portion engage with an inner wall of the air flowing pipe and an outer wall of the cartridge respectively; the sealing plug seals a gap between an outer wall of the air flowing pipe and an inner wall of the cartridge, and the plate is located between the sealing cover and the sealing plug; and a third opening and a fourth opening of the liquid injection channel are defined in the plate and the sealing plug respectively.

Preferably, a protruding portion protrudes from the sealing cover towards the plate, and a first positioning hole allowing the protruding portion to be clamped thereinto is defined in the plate; and an extending portion extending towards the plate is formed on an outer ring of the second opening, and a first recessed portion corresponding to the extending portion is formed on an outer ring of the third opening.

Preferably, the atomizer device further includes an air inlet assembly arranged on one end of the atomizer device opposite to the sealing unit, and the air inlet assembly communicates with the air flowing pipe; the air inlet assembly includes an air inlet tube and a second adjusting ring rotatably arranged on an outer ring of the air inlet tube; an air inlet hole unit is formed in a circumference of the air inlet tube for allowing air to flow into the air inlet tube; a second adjusting opening corresponding to the air inlet hole unit is arranged in the second adjusting ring; and a rotation of the second adjusting ring enables the second adjusting opening to adjust an area of a portion of the air inlet hole unit which allows air to flow into the air inlet tube.

Preferably, the air inlet hole unit includes a plurality of second air inlets arranged along a circumference of the air inlet tube, and the second air inlets are of different areas; an area of the second adjusting opening is no less than that of the largest second air inlet; and a rotation of the second adjusting ring enables the second adjusting opening to communicate with the corresponding second air inlet.

Preferably, the air inlet hole unit includes a plurality of third air inlets arranged along the circumference of the air inlet tube; the second adjusting opening includes a second recessed portion formed in an inner wall of the second adjusting ring, and the second recessed portion extends to an end surface of the second adjusting ring; two boundaries of the second recessed portion in a circumferential direction of the second adjusting ring correspond to two end boundaries of the third air inlets in a circumferential direction of the air inlet tube; and the second adjusting ring is rotated to adjust an area of a portion of the third air inlets which communicates with the second recessed portion.

Preferably, an elastic column protrudes from a side wall of the air inlet tube, a plurality of clamping mechanisms engageable with the elastic column are formed in an inner ring of the second adjusting ring along a circumference of the second adjusting ring.

Preferably, the atomizer device further includes a suction nozzle assembly; the suction nozzle assembly includes a fixing member and a first adjusting ring; the fixing member includes a cylindrical body engages with an inner ring of the plate to communicate with the air flowing pipe; a first air inlet is defined in a side wall of the cylindrical body, the first adjusting ring is rotatably arranged on an outer ring of the cylindrical body, a first adjusting opening corresponding to the first air inlet is defined in the first adjusting ring, and the first adjusting ring is rotated to adjust an area of an opening of the first air inlet which communicates with atmosphere.

Preferably, the atomizer device further includes an atomizer cover, an atomizer base, and an atomizer assembly; the atomizer cover is covered on one end of the liquid reservoir chamber corresponding to the sealing unit, and a liquid outlet is defined in the atomizer cover allowing liquid to flow out of the liquid reservoir chamber; the atomizer base engages with the atomizer cover, and the atomizer assembly is located between the atomizer base and the atomizer cover; a through hole is defined in a middle portion of the atomizer base; the atomizer assembly includes a heating coil made of ceramics, and an inner hole of the heating coil respectively communicate with the air flowing pipe and the through hole; two silicone covers are respectively covered on outer rings of two opposite ends of the heating coil, such that a middle portion of the heating coil forms a liquid absorbing portion capable of absorbing the liquid solution flowing out of the liquid reservoir chamber through the liquid outlet.

Preferably, the cartridge, the air flowing pipe, and the atomizer cover are made of ceramics.

Preferably, the atomizer device further includes a suction nozzle circumferentially engaging with the adjusting valve; the adjusting valve includes a adjusting cover and a sealing cover arranged on one side of the sealing cover corresponding to the sealing unit, and the sealing cover circumferentially engages with the adjusting cover; the first opening penetrates the adjusting cover and the sealing cover; the suction nozzle is rotated to drive the adjusting valve to rotate between the first position and the second position, thereby opening or closing the liquid injection channel.

Preferably, the suction nozzle is clamped to the adjusting cover to enable a circumferential positioning of the suction nozzle and the adjusting cover; the suction nozzle is movable along an axial direction to engage with the adjusting cover or disengage from the adjusting cover; an elastic member is arranged between the suction nozzle and the adjusting cover to provide an elasticity for keeping the suction nozzle from disengaging from the adjusting cover.

The electronic cigarette provided in the present disclosure has the atomizer device as stated above.

The adjusting valve of the atomizer device and the electronic cigarette of the present disclosure is movable between the first position and the second position, such that the first opening is capable of opening or closing the liquid injection channel to facilitate the injection of the liquid solution; in addition, since the liquid solution can be injected without removing the suction nozzle, the injection of the liquid solution is convenient and simplified and the situation that the suction nozzle gets dirty or get lost also can be avoided.

BRIEF DESCRIPTION OF THE DRAWINGS

The present disclosure will be described in more detail with reference to the accompany drawings and the embodiments, wherein in the drawings.

PREFERRED EMBODIMENTS

For clearly understanding technical features, purpose, and effect of the present disclosure, embodiments are given in detail hereinafter with reference to the accompanying drawings.

Figure 1:
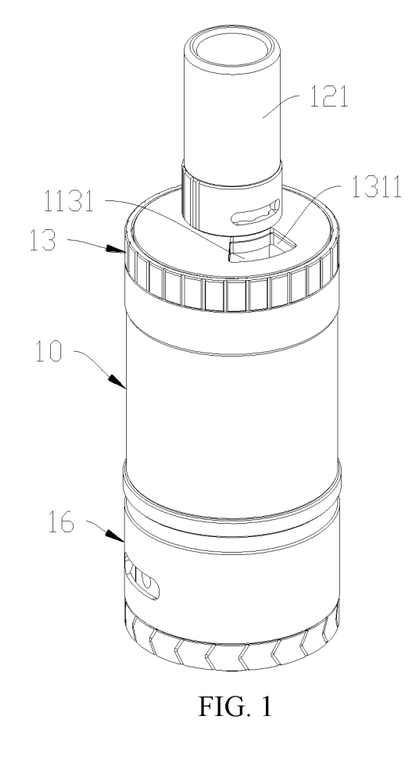
FIG. 1 is a schematic view showing an adjusting valve of an atomizer device of an electronic cigarette is in a first position in accordance with an embodiment of the present disclosure.
Figure 2:
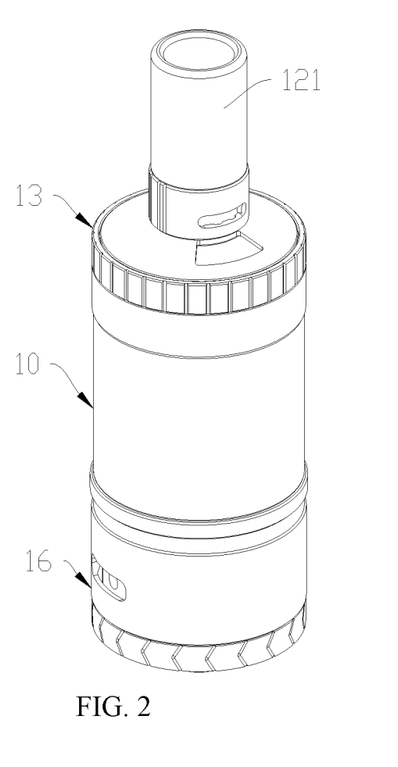
FIG. 2 is a schematic view showing the adjusting valve of FIG. 1 is in a second position.
Figure 3:
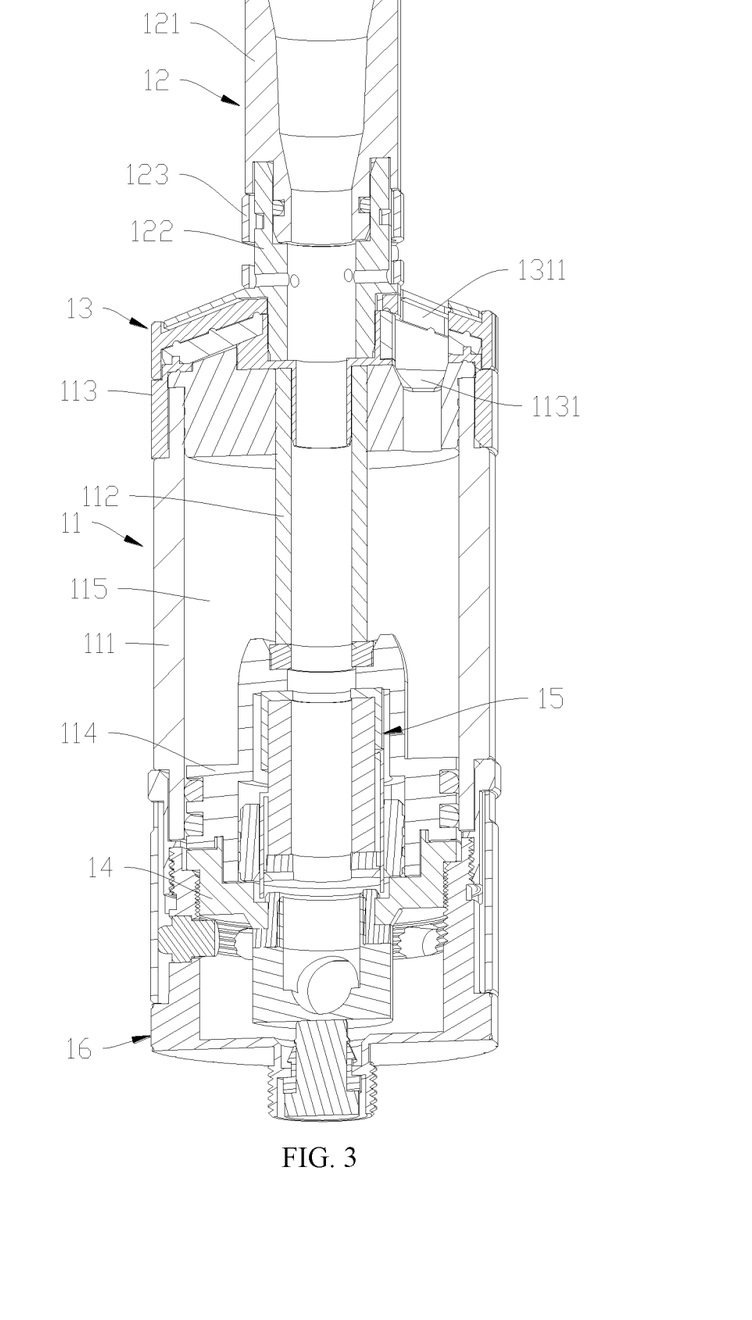
FIG. 3 is a cross-sectional view of the atomizer device of FIG. 1.

Referring to FIGS. 1 to 3, an electronic cigarette in accordance with an embodiment of the present disclosure includes an atomizer device 10 and a battery device. The battery device supplies electric energy to the atomizer device 10 such that the atomizer device 10 can work to heat and atomize liquid solution injected into the electronic cigarette. The atomizer device 10 includes a liquid reservoir assembly 11, a suction nozzle assembly 12, an adjusting valve 13, an atomizer base 14, an atomizer assembly 15, and an air inlet assembly 16.

Referring to FIGS. 3 to 6, in some embodiments, the liquid reservoir assembly 11 includes a cartridge 111, an air flowing pipe 112, a sealing unit 113, and an atomizer cover 114. The cartridge 111 is sleeved on the air flowing pipe 112, and a liquid reservoir chamber 115 is formed between the cartridge 111 and the air flowing pipe 112. The sealing unit 113 and the atomizer cover 114 respectively cover two opposite ends of the liquid reservoir chamber 115 and keep the air flowing pipe 112 communicating with atmosphere. A first sealing rubber gasket is arranged between the atomizer cover 114 and the cartridge 111, and a second sealing rubber gasket is arranged between the atomizer cover 114 and the air flowing pipe 112. The cartridge 111, the air flowing pipe 112, the sealing unit 113, and the atomizer cover 114 cooperate with each other to form a housing with the liquid reservoir chamber 115. A liquid injection channel 1131 is defined in the sealing unit 113, such that liquid solution can be injected into the liquid reservoir chamber 115 through the liquid injection channel 1131. A liquid outlet 1141 is defined in the atomizer cover 114, thus, the liquid solution can flow out of the liquid reservoir chamber 115 through the liquid outlet 1141. In other embodiments, the liquid injection channel 1131 can be defined in the cartridge 111 or other components of the atomizer device 10; and the sealing unit 113, the cartridge 111, and the air flowing pipe 112 can be integrally formed, thus, the sealing unit 113 forms an end wall of the liquid reservoir chamber 115.

Figure 4:
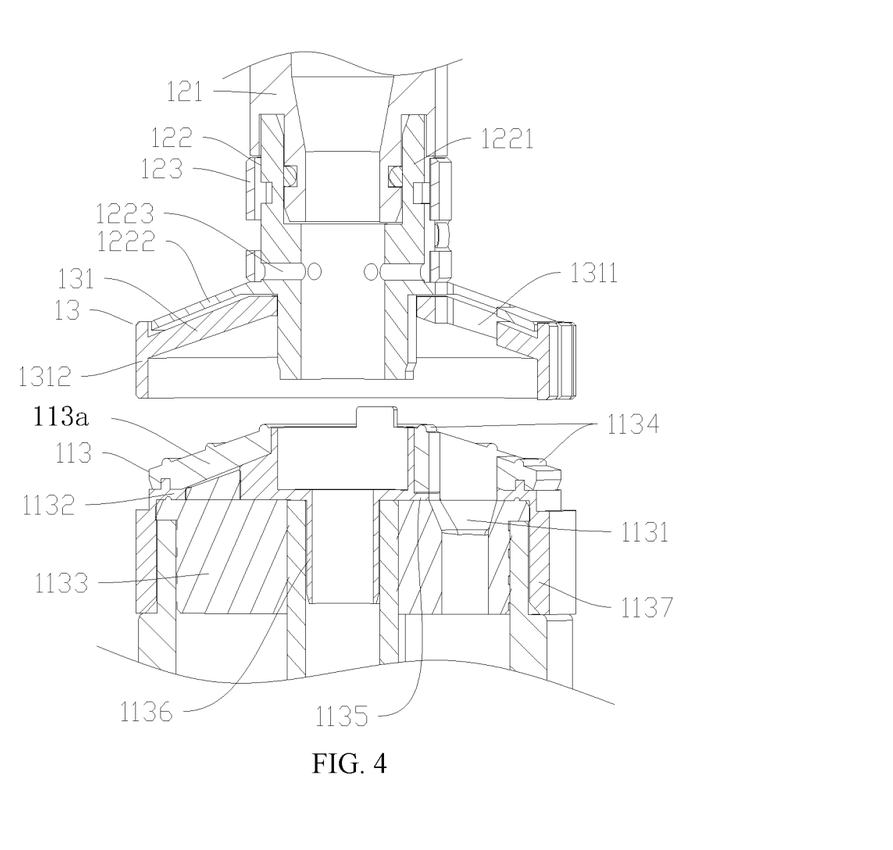
FIG. 4 is a cross-sectional view of a suction nozzle assembly, the adjusting valve, and a liquid reservoir assembly of FIG. 3 which are in a disassembled state.
Figure 7:
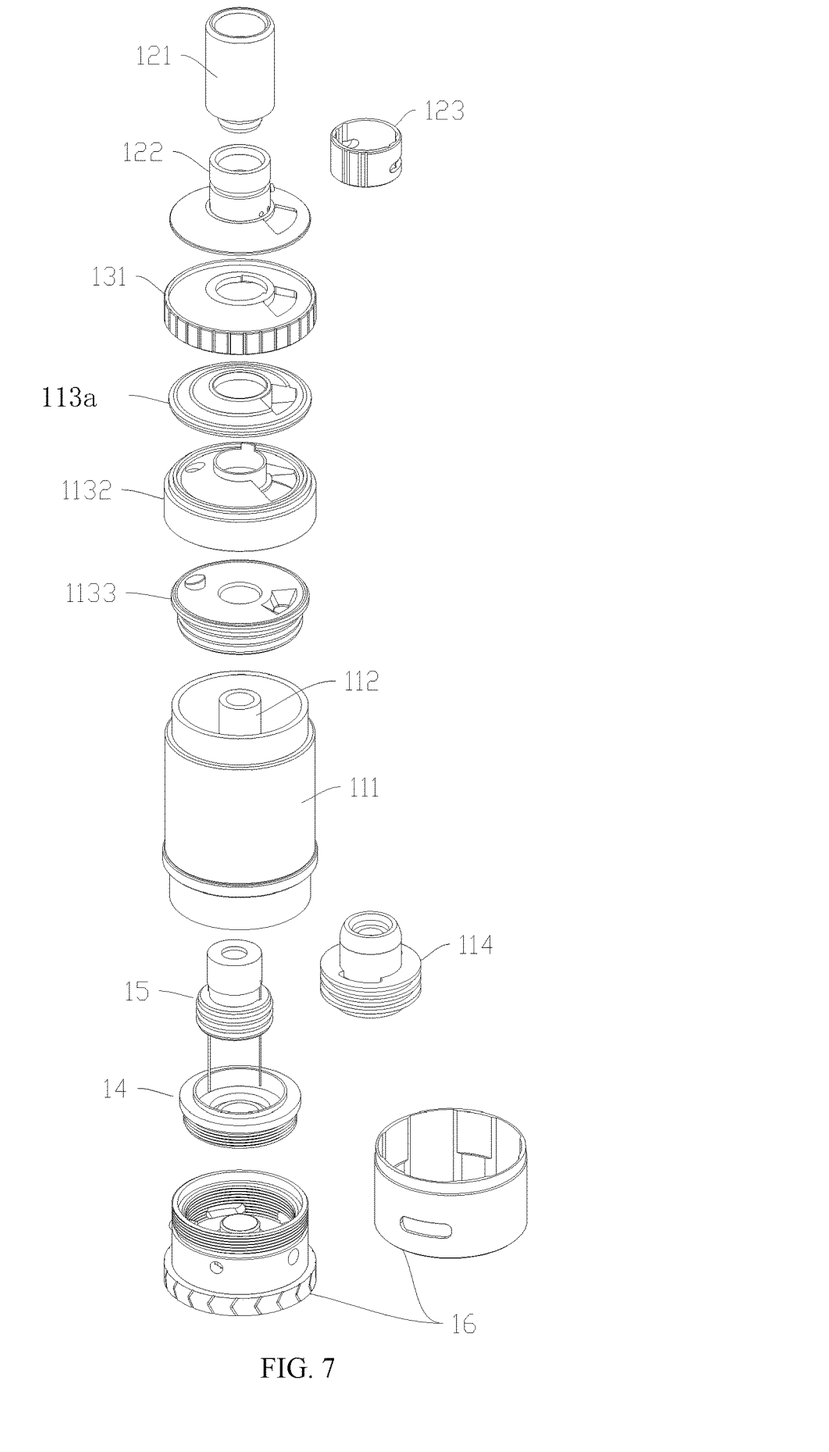
FIG. 7 is an exploded view of the atomizer device of FIG. 1.
Figure 8:
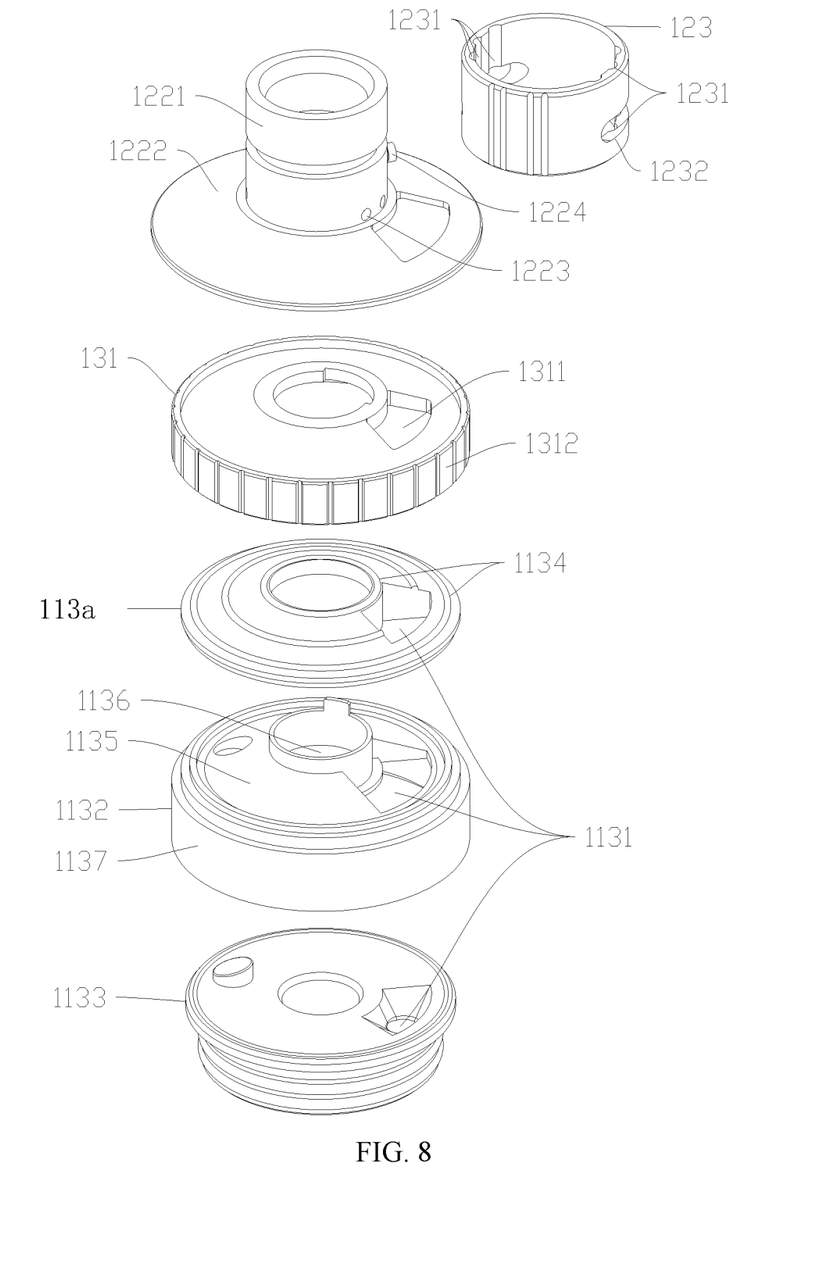
FIG. 8 is an exploded view of the suction nozzle assembly, the adjusting valve, and a sealing unit of FIG. 7.

Referring to FIGS. 4, 7, and 8, the suction nozzle assembly 12 includes a suction nozzle 121, a fixing member 122, and a first adjusting ring 123. The fixing member 122 is arranged between the suction nozzle 121 and the sealing unit 113. The suction nozzle 121, the fixing member 122, and the air flowing pipe 112 communicate with each other. The fixing member 122 includes a cylindrical body 1221 and an annular abutting portion 1222 arranged on an outer wall of the cylindrical body 1221. The abutting portion 1222 abuts the adjusting valve 13 against the sealing unit 113.

In some embodiments, the adjusting valve 13 includes an annular adjusting cover 131. The adjusting cover 131 is rotatably sleeved on the cylindrical body 1221, and is located between the sealing unit 113 and the abutting portion 1222, correspondingly engaging with the sealing unit 113. The adjusting cover 131 contacts the sealing unit 113, and is capable of rotating between a first position and a second position across a surface of the sealing unit 113. A first opening 1311 is defined in the adjusting cover 131. In some embodiments, the adjusting cover 131 may include a rotating ring 1312 arranged on an outer ring of the adjusting cover 131; anti-skid designs may be provided on an outer wall of the rotating ring 1312, thus, an external force may be applied to the rotating ring 1312 to rotate the adjusting cover 131. In other embodiments, the adjusting cover 131 may be located on an inner wall of the liquid reservoir chamber 115 to engage with an inner wall of the sealing unit 113, and the adjusting cover 131 may be driven to rotate by other means.

When the adjusting cover 131 is in the first position, the first opening 1311 communicates with the liquid injection channel 1131 to open the liquid injection channel 1131; when the adjusting cover 131 is in the second position, the first opening 1311 misaligns with the liquid injection channel 1131 to close the liquid injection channel 1131. In other embodiments, the adjusting cover 131 may slidably engage with the sealing unit 113, and the adjusting cover 131 can slide back and forth to correspondingly open or close the liquid injection channel 1131.

In some embodiments, a first air inlet 1223 is defined in a side wall of the cylindrical body 1221. The first adjusting ring 123 is rotatably sleeved on the cylindrical body 1221, and is adjacent to one side of the abutting portion 1222 facing away from the adjusting cover 131. A first adjusting opening 1231 is defined in the first adjusting ring 123, corresponding to the first air inlet 1223. When the first adjusting ring 123 is rotated, the first adjusting opening 1231 adjusts an area of an opening of the first air inlet 1223 which communicates with atmosphere, thus, the amount of air flowing into the suction nozzle 121 can be adjusted and thus the temperature of the smoke at the suction nozzle 121 can be correspondingly adjusted. A restricting portion 1224 is arranged on the side wall of the cylindrical body 1221, and a restricting slot 1232 corresponding to the restricting portion 1224 is defined in the first adjusting ring 123. The restricting portion 1224 engages with the restricting slot 1232 to restrict the rotating angle of the cylindrical body 1221.

In some embodiments, the sealing unit 113 includes a sealing cover 113a, a fastening member 132, and a sealing plug 1133. The sealing cover 113a is made of flexible rubber such as silicone. A second opening of the liquid injection channel 1131 is defined in the sealing cover 113a. A sealing ring 1134 protrudes from a surface of the sealing cover 113a, corresponding to the adjusting cover 131. The sealing ring 1134 forms an enclosed structure around the second opening, being capable of preventing the leakage of the liquid solution through a gap between the sealing cover 113a and the adjusting cover 131. In addition, the sealing ring 1134 reduces the contacting area between the adjusting cover 131 and the sealing cover 113a, thereby facilitating the rotation of the adjusting cover 131.

In some embodiments, the fastening member 1132 includes an annular plate 1135, a first sleeving portion 1136 arranged in an inner ring of the plate 1135, and a second sleeving portion 1137 arranged on an outer ring of the plate 1135. The first sleeving portion 1136 engages with an inner wall of the corresponding end of the air flowing pipe 112 and the second sleeving portion 1137 engages with an outer wall of the corresponding end of the cartridge 111, thus, the sealing unit 113 can be fastened to the cartridge 111 and the air flowing pipe 112. The cylindrical body 1221 engages with the inner ring of the plate 1135 to communicate with the air flowing pipe 112, thus, smoke can flow through the cylindrical body 1221.

In some embodiments, the sealing plug 1133 is also made of flexible rubber such as silicone. The sealing plug 1133 seals a gap between an outer wall of the air flowing pipe 112 and an inner wall of cartridge 111, and the plate 1135 is located between the sealing cover 113a and the sealing plug 1133. A third opening and a fourth opening of the liquid injection channel 1131 are defined in the plate 1135 and the sealing plug 1133, respectively.

In some embodiments, a protruding portion is arranged on the sealing plug 1133, extending towards the plate 1135. A first positioning hole is defined in the plate 1135, corresponding to the protruding portion. The protruding portion is clamped into the first positioning hole, thereby enabling the circumferential positioning of the sealing plug 1133 and the fastening member 1132. An extending portion is arranged on an outer ring of the second opening and extends towards the plate 1135. A first recessed portion corresponding to the extending portion is formed on an outer ring of the third opening. The extending portion engages with the first recessed portion to enable the circumferential positioning of the sealing plug 1133 and the fastening member 1132.

Figure 5:
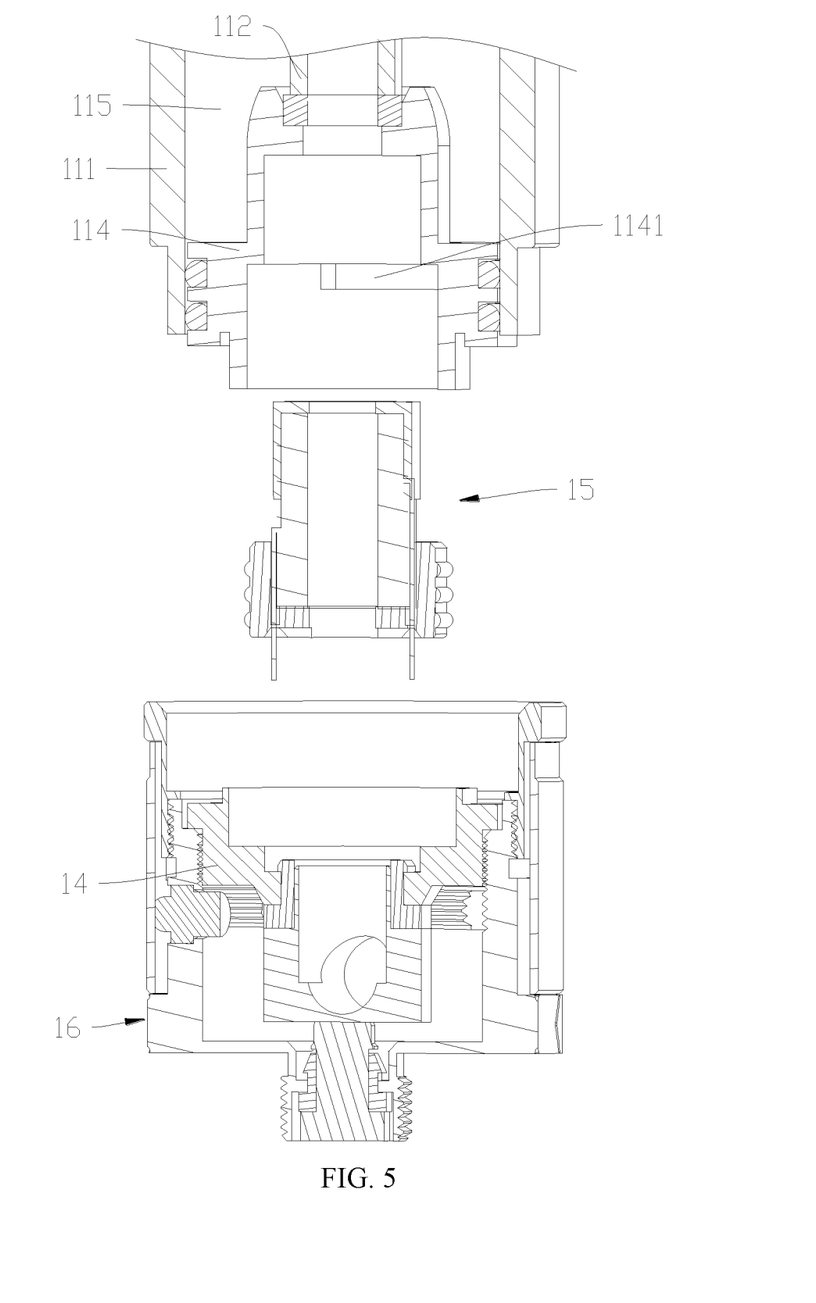
FIG. 5 is a cross-sectional view of the liquid reservoir assembly, an atomizer assembly, an atomizer base, and an air inlet assembly of FIG. 3 which are in a disassembled state.
Figure 6:
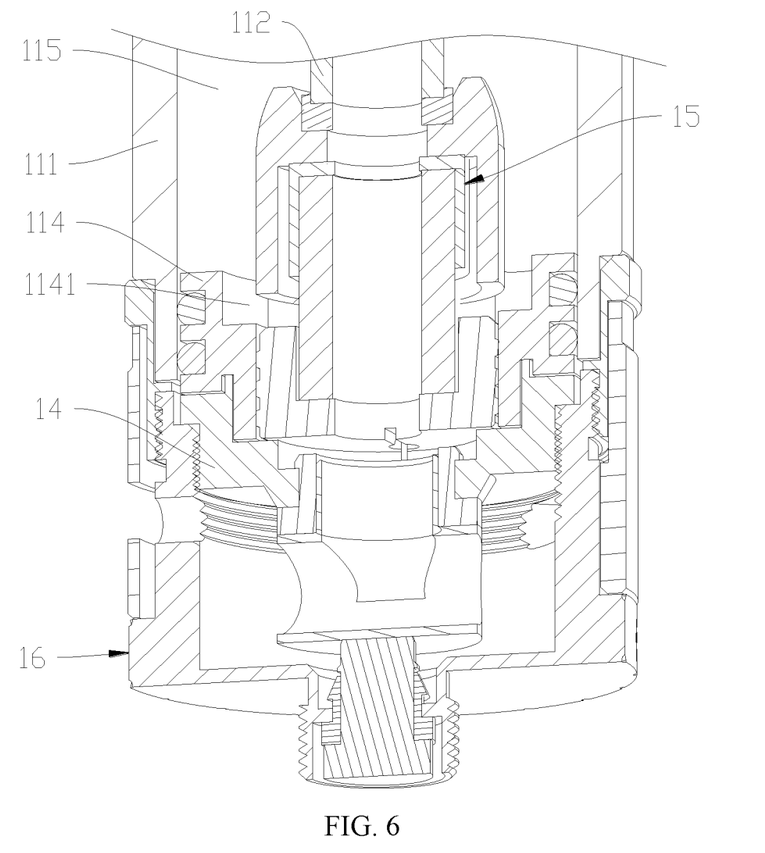
FIG. 6 is a partial cross-sectional view of the atomizer device of FIG. 1 after the atomizer device is rotated to another position.
Figure 9:
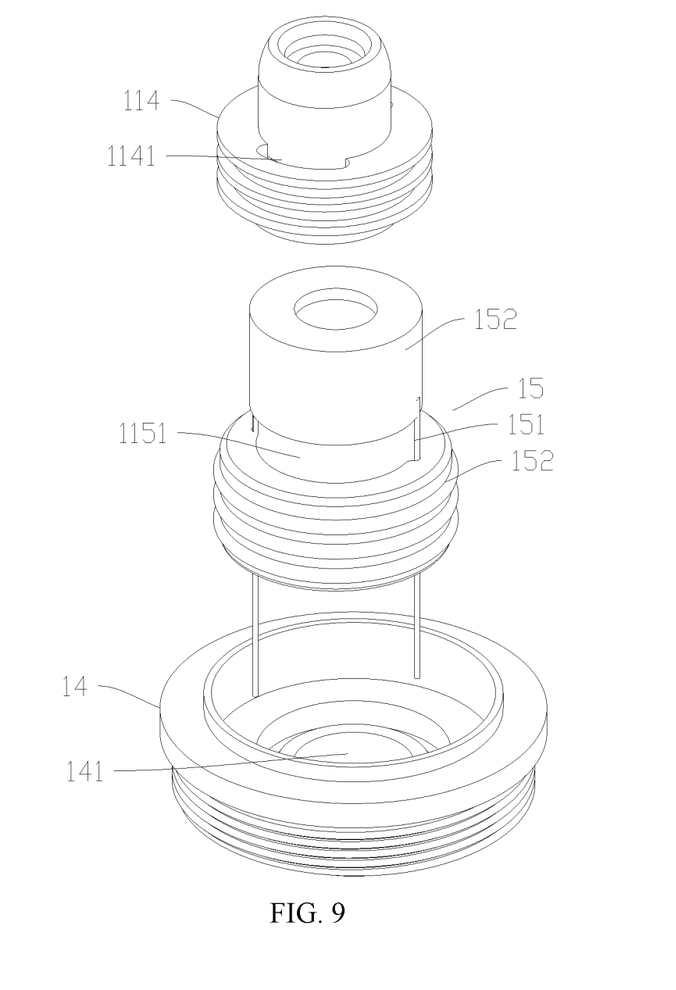
FIG. 9 is an exploded view of an atomizer cover, the atomizer assembly, and the atomizer base of FIG. 7.

Referring to FIGS. 5, 7, and 9, the atomizer base 14 engages with the atomizer cover 114, and the atomizer assembly 15 is located between the atomizer base 14 and the atomizer cover 114. The atomizer assembly 15 includes a cylindrical heating coil 151 made of ceramics. An inner hole of the heating coil 151 communicates with the air flowing pipe 112. A through hole 141 communicating with the inner hole of the heating coil 151 is defined in a middle portion of the atomizer base 14, such that air flow can flow into the inner hole of the heating coil 151.

In some embodiments, two silicone covers 152 are arranged on outer rings of the two opposite ends of the heating coil 151 respectively, such that a middle portion of the heating coil 151 forms a liquid absorbing portion 1511 which absorbs the liquid solution flowing out through the liquid outlet 1141. The heating coil 151 is heated after conducted to the battery device to atomize the liquid solution. The smoke flows towards the suction nozzle 121 through the air flowing pipe 112.

The silicone covers 152 perform a sealing function between the corresponding end of the heating coil 152 and the atomizer cover 114/the atomizer base 14, preventing the leakage of the liquid solution through the inner hole of the heating coil 152. In addition, the arranged position of the silicone cover 152 can be adjusted to control the amount of the liquid solution flowing into the heating coil 152, which prevents too much liquid solution from flowing into the heating coil 152. Thus, leakage of the liquid solution caused by incomplete atomization of the liquid solution can be avoided.

In some embodiments, the cartridge 111, the air flowing pipe 112, and the atomizer cover 114 are made of ceramics. Thus, before the liquid solution injected into the electronic cigarette gets heated by the heating coil 151, the liquid solution only contacts the components of the electronic cigarette which are made of ceramics and silicone rather than metal or plastic. Thus, the situation that harmful ingredients from metal or plastic affect the user's health can be avoided.

Figure 10:
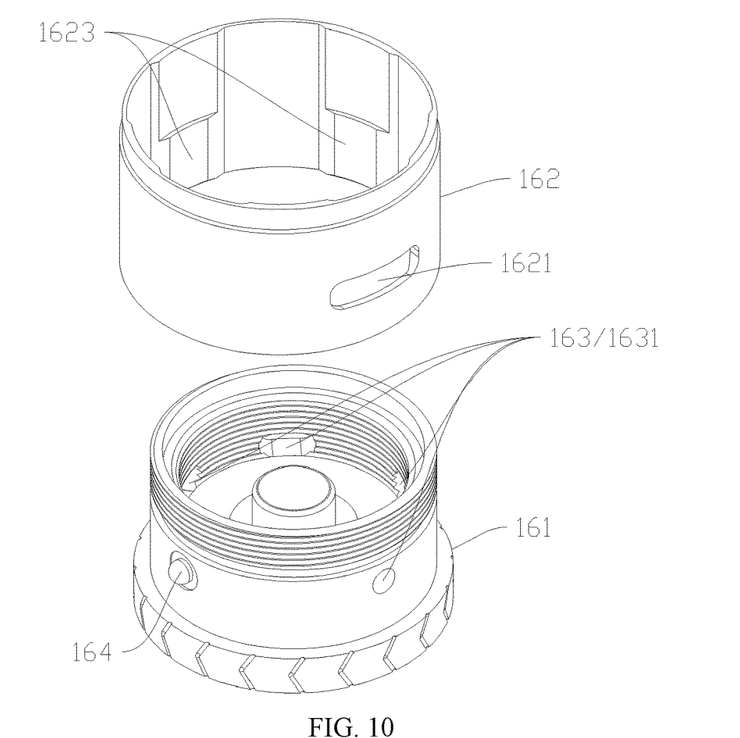
FIG. 10 is an exploded view of the air inlet assembly of FIG. 7.

Referring to FIGS. 5, 7, and 10, the air inlet assembly 16 is arranged on one end of the atomizer device 10 opposite to the sealing unit 113. The air inlet assembly 16 communicates with the air flowing pipe 112. The air inlet assembly 16 includes an air inlet tube 161 and a second adjusting ring 162 rotatably arranged on an outer ring of the air inlet tube 161. The air inlet tube 161 engages with the atomizer base 14, such that the air inlet tube 161 can communicate with the through hole 141 of the atomizer base 14. In other embodiments, the air inlet tube 161 can directly communicate with the inner hole of the heating coil 151.

In some embodiments, an air inlet hole unit 163 is formed in a circumference of the air inlet tube 161, allowing air to flow into the air inlet tube 161. The air inlet tube 161 engages with the atomizer base 14, such that the air flowing into the air inlet tube 161 can flow into the inner hole of the heating coil 151.

A second adjusting opening 1621 is defined in the second adjusting ring 162, corresponding to the air inlet hole unit 163. The rotation of the second adjusting ring 162 adjusts an area of a portion of the air inlet hole unit 163 which allowing air to flow into the air inlet tube 161, thus, the amount of air flowing into the electronic cigarette and the amount of the smoke sucked by a user of the electronic cigarette can be adjusted.

Referring to FIG. 10, in some embodiments, the air inlet unit 163 includes a plurality of second air inlets 1631 arranged on the circumference of the air inlet tube 161. The air inlets 1631 are of different areas. An area of the second adjusting opening 1621 is no less than that of the largest second air inlet 1631. The rotation of the second adjusting ring 162 enables the second adjusting opening 1621 to communicate with different second air inlets 1631 of different areas respectively, thus, air can flow into the air inlet tube 161 through the corresponding second air inlet 1631 to enable the adjusting of the amount of air flowing into the electronic cigarette.

Figure 11:
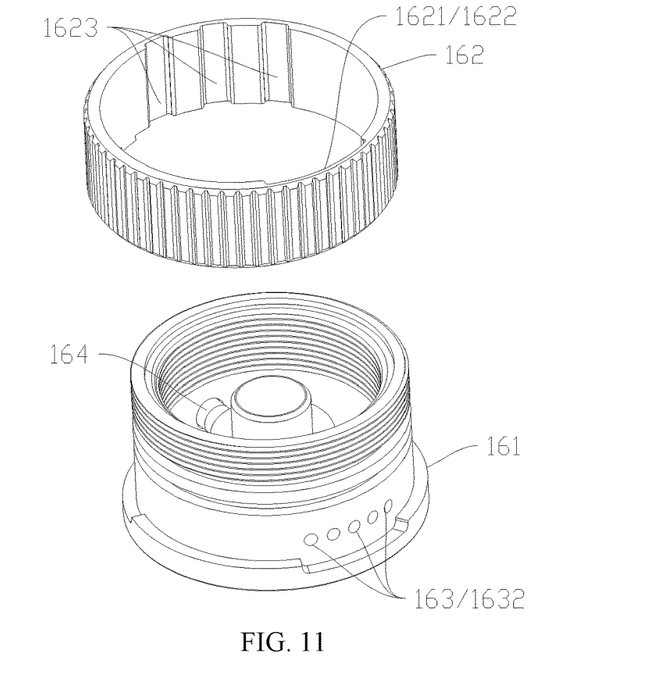
FIG. 11 is an exploded view of an air inlet assembly in accordance with other embodiments of the present disclosure.

Referring to FIG. 11, in other embodiments, the air inlet unit 163 can include a number of third air inlets 1632 arranged on the circumference of the air inlet tube 161. A second recessed portion 1622 is formed on an inner wall of the second adjusting ring 162, and the second recessed portion 1622 extends to an end surface of the second adjusting ring 162. Two boundaries of the second recessed portion 1622 in the circumferential direction of the second adjusting ring 162 respectively correspond to two end boundaries of the third air inlets 1632 in the circumferential direction of the air inlet tube 161. The second adjusting valve 162 can be rotated to adjust an area of a portion of the third air inlets 1632 communicating with the second recessed portion 1622. For example, the second adjusting ring 162 can be rotated to different positions such that air can flow into the atomizer device through the corresponding third air inlet 1632 communicating with the second recessed portion 1622, thus, the amount of air flowing into the air inlet tube 161 can be adjusted.

Referring to FIGS. 10 and 11, in order to ensure the accuracy of the rotating position of the second adjusting valve 162 and ensure the positioning of the second adjusting valve 162 after the second adjusting valve 162 is rotated, an elastic column 164 is arranged on the outer wall of the air inlet tube 161, and a number of clamping mechanisms 1623 engageable with the elastic column 164 are formed in an inner ring of the second adjusting ring 162 along a circumference of the second adjusting valve 162. The elastic column 164 engages with the corresponding clamping mechanism 1623, thereby enabling the positioning of the second adjusting ring 162.

Figure 12:
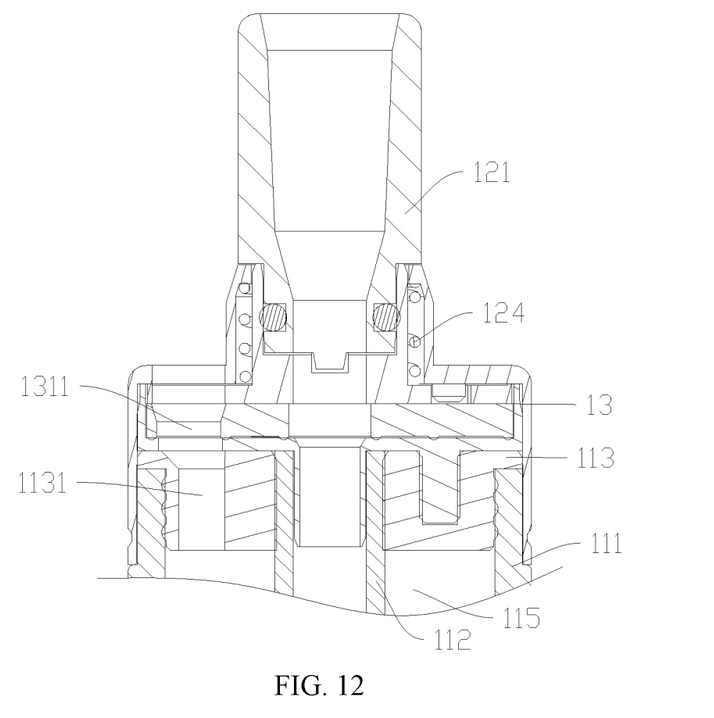
FIG. 12 is a cross-sectional view of a suction nozzle, a adjusting valve, and a liquid reservoir assembly which are in an assembled state in accordance with other embodiments of the present disclosure.
Figure 13:
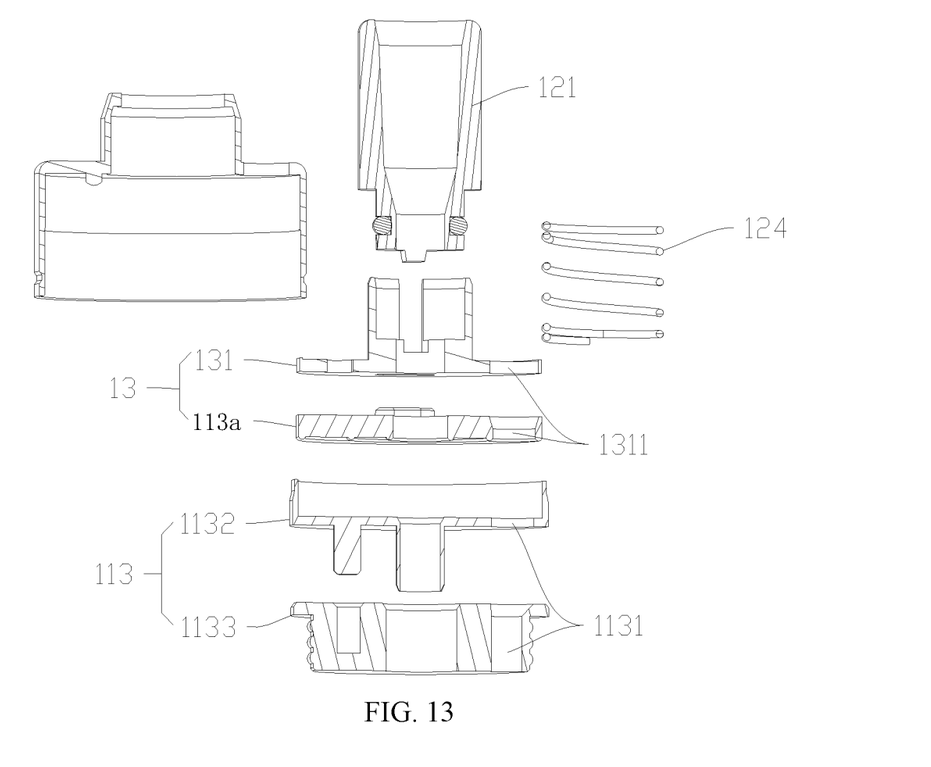
FIG. 13 is an exploded view of the suction nozzle, the adjusting valve, and a sealing unit of FIG. 12.

Referring to FIGS. 12 and 13, in other embodiments, the suction nozzle 121 can be clamped to the adjusting valve 13, and the adjusting valve 13 can be driven to rotate between the first position and the second position by the suction nozzle 121. For example, the adjusting valve 13 may include the adjusting cover 131 and the sealing cover 113a located between the adjusting cover 131 and the sealing unit 113; a first protrusion is arranged on the sealing cover 113a, and a second positioning hole is defined in the adjusting cover 131, corresponding to the first protrusion; and the first protrusion engages with the second positioning hole to enable the circumferential positioning of the sealing cover 113a and the adjusting cover 131.

The rotation of the suction nozzle 121 drives the adjusting cover 131 and the sealing cover 113a to simultaneously rotate between the first position and the second position. The first opening 1311 penetrates the adjusting cover 131 and the sealing cover 113a and corresponds to the liquid injection channel 1131 of the sealing unit 113. When the adjusting valve 13 is in the first position, the first opening 1311 communicates with the liquid injection channel 1131, thus, the liquid injection channel 1131 is opened; when the adjusting valve 13 is in the second position, the first opening 1311 misaligns with the liquid injection channel 1131, thus, the liquid injection channel 1131 is closed.

In some embodiments, a second protrusion is arranged on the suction nozzle 121 and a clamping slot is correspondingly defined in the adjusting cover, and the second protrusion can be clamped into the clamping slot to enable the circumferential positioning of the suction nozzle 121 and the adjusting cover 131. The suction nozzle 121 is capable of moving back and forth along an axial direction to be clamped into the adjusting cover 131 or to disengage from the adjusting cover 131. When liquid injection is required, the suction nozzle 121 is pushed inwards to engage with the adjusting cover 131 and thus drives the adjusting valve 13 to rotate to the first position to open the liquid injection channel 1131. After the liquid injection is finished, the suction nozzle 121 is rotated to drive the adjusting valve 13 to rotate to the second position, and then the suction nozzle 121 is slid outwards to disengage from the adjusting cover 131. An elastic member 124 is arranged between the suction nozzle 121 and the adjusting cover 131. The elastic member 124 is configured to provide an elasticity to keep the suction nozzle 121 from disengaging from the adjusting cover 131, thus, mis-opening of the liquid injection channel 1131 caused by mis-rotation of the adjusting cover 131/the suction nozzle 121 can be avoided.

The contents described above are only preferred embodiments of the present disclosure, but the scope of the present disclosure is not limited to the embodiments. Any ordinarily skilled in the art would make any modifications or replacements to the embodiments in the scope of the present disclosure, and these modifications or replacements should be included in the scope of the present disclosure. Thus, the scope of the present disclosure should be subjected to the claims.

What is claimed is:

1. An atomizer device, wherein the atomizer device comprises a housing, a liquid reservoir chamber (115) defined in the housing, and an adjusting valve (13) engaging with the housing; a liquid injection channel (1131) is defined on the housing for injecting liquid solution into the liquid reservoir chamber (115); the adjusting valve (13) is movable between a first position and a second position and keeps connected to the housing while moving relative to the housing; the adjusting valve (13) is able to move to the first position to open the liquid injection channel (1131), and is able to move to the second position to close the liquid injection channel (1131); the atomizer device comprises an air flowing passage (112) and a sealing unit (113) sealing one end of the liquid reservoir chamber (115).

2. The atomizer device of claim 1, wherein the atomizer device comprises a cartridge (111) sleeved on the air flowing passage (112), and the sealing unit (113) is arranged on one end of the cartridge (111) corresponding to the air flowing passage (112); the liquid reservoir chamber (115) is defined between the cartridge (111) and the air flowing passage (112).

3. The atomizer device of claim 1, wherein the liquid injection channel (1131) is defined on the sealing unit (113); the sealing unit (113) comprises a sealing cover (113a) correspondingly engaging with the adjusting valve (13), and a second opening of the liquid injection channel (1131) is defined in the sealing cover (113a); and the adjusting valve (13) comprises an adjusting cover (131) movably contacting the sealing cover (113a).

4. The atomizer device of claim 3, wherein a driving member (1312) is arranged on an outer periphery of the adjusting cover (131) for driving the adjusting cover (131) to move, and an outer surface of the driving member (1312) is provided with anti-skid structures.

5. The atomizer device of claim 3, wherein a sealing member (1134) protrudes from one side of the sealing cover (113a) corresponding to the adjusting cover (131), and the sealing member (1134) forms an enclosed structure around the second opening.

6. The atomizer device of claim 3, wherein the sealing unit (113) comprises a fastening member (1132) and a sealing plug (1133); the fastening member (1132) comprises a plate (1135), a first sleeving portion (1136) arranged on an inner periphery of the plate (1135), and a second sleeving portion (1137) arranged on an outer periphery of the plate (1135); the first sleeving portion (1136) and the second sleeving portion (1137) engage with an inner wall of the air flowing passage (112) and an outer wall of a cartridge (111) respectively; the sealing plug (1133) seals a gap between an outer wall of the air flowing passage (112) and an inner wall of a cartridge (111), and the plate (1135) is located between the sealing cover (113a) and the sealing plug (1133); and a third opening and a fourth opening of the liquid injection channel (1131) are defined in the plate (1135) and the sealing plug (1133) respectively.

7. The atomizer device of claim 6, wherein a protruding portion protrudes from the sealing plug (1133) towards the plate (1135), and a first positioning hole allowing the protruding portion to be clamped thereinto is defined in the plate (1135); and an extending portion extending towards the plate (1135) is formed on an outer periphery of the second opening, and a first recessed portion corresponding to the extending portion is formed on an outer periphery of the third opening.

8. The atomizer device of claim 1, wherein the atomizer device further comprises an air inlet assembly (16) arranged on one end of the atomizer device opposite to the sealing unit (113), and the air inlet assembly (16) communicates with the air flowing passage (112); the air inlet assembly (16) comprises an air inlet member (161) and a second adjusting member (162) rotatably sleeved on the air inlet member (161); an air inlet hole unit (163) is defined in a circumference of the air inlet member (161) for allowing air to flow into the air inlet member (161); a second adjusting opening (1621) corresponding to the air inlet hole unit (163) is arranged in the second adjusting member (162); and a rotation of the second adjusting member (162) enables the second adjusting opening (1621) to adjust an area of a portion of the air inlet hole unit (163) which allows air to flow into the air inlet member (161).

9. The atomizer device of claim 8, wherein the air inlet hole unit (163) comprises a plurality of second air inlets (1631) arranged along a circumference of the air inlet member (161), and the second air inlets (1631) are of different areas; an area of the second adjusting opening (1621) is no less than that of the largest second air inlet (1631); and a rotation of the second adjusting member (162) enables the second adjusting opening (1621) to communicate with the corresponding second air inlet (1631).

10. The atomizer device of claim 8, wherein the air inlet hole unit (163) comprises a plurality of third air inlets (1632) arranged along the circumference of the air inlet member (161); the second adjusting opening (1621) comprises a second recessed portion (1622) formed in an inner wall of the second adjusting member (162), and the second recessed portion (1622) extends to an end surface of the second adjusting member (162); two boundaries of the second recessed portion (1622) in a circumferential direction of the second adjusting member (162) correspond to two end boundaries of the third air inlets (1632) in a circumferential direction of the air inlet member (161); the second adjusting member (162) is rotated to adjust an area of a portion of the third air inlets (1632) which communicates with the second recessed portion (1622).

11. The atomizer device of claim 8, wherein an elastic column (164) protrudes from a side wall of the air inlet member (161), a plurality of clamping mechanisms (1623) engageable with the elastic column (164) are formed in an inner periphery of the second adjusting member (162) along a circumference of the second adjusting member (162).

12. The atomizer device of claim 1, wherein the atomizer device further comprises a suction nozzle assembly (12); the suction nozzle assembly (12) comprises a fixing member (122) and a first adjusting member (123); the fixing member (122) comprises a cylindrical body (1221) engages with an inner periphery of the plate (1135) to communicate with the air flowing passage (112); a first air inlet (1223) is defined in a side wall of the cylindrical body (1221), the first adjusting member (123) is rotatably arranged on an outer periphery of the tubular body (1221), a first adjusting opening (1231) corresponding to the first air inlet (1223) is defined in the first adjusting member (123), and the first adjusting member (123) is able to be rotated to adjust an area of an opening of the first air inlet (1223) which communicates with atmosphere.

13. The atomizer device of claim 1, wherein the atomizer device further comprises an atomizer cover (114), an atomizer base (14), and an atomizer assembly (15); the atomizer cover (114) is covered on one end of the liquid reservoir chamber (115) corresponding to the sealing unit (113), and a liquid outlet (1141) is defined in the atomizer cover (114) allowing liquid to flow out of the liquid reservoir chamber (115); the atomizer base (14) engages with the atomizer cover (114), and the atomizer assembly (15) is located between the atomizer base (14) and the atomizer cover (114); a through hole is defined in a middle portion of the atomizer base (14); the atomizer assembly (15) comprises a heating member (151), and an inner hole of the heating member (151) respectively communicate with the air flowing passage (112) and the through hole; two covers are respectively covered on an outer periphery of two opposite ends of the heating member (151), such that a middle portion of the heating member (151) forms a liquid absorbing portion (1511) capable of absorbing the liquid solution flowing out of the liquid reservoir chamber (115) through the liquid outlet (1141).

14. The atomizer device of claim 1, wherein the atomizer device further comprises a suction nozzle (121) circumferentially engaging with the adjusting valve (13); the adjusting valve (13) comprises an adjusting cover (131) and a sealing cover (113*a*) arranged on one side of the adjusting cover (131) corresponding to the sealing unit (113), and the sealing cover (113*a*) circumferentially engages with the adjusting cover (131); a first opening (1311) corresponding to the liquid injection channel (1131) is defined in the adjusting valve (13); the first opening (1311) extends through the adjusting cover (131) and the sealing cover (113*a*); the suction nozzle (121) is adapted to drive the adjusting valve (13) to move between the first position and the second position, thereby opening or closing the liquid injection channel (1131).

15. The atomizer device of claim 14, wherein the suction nozzle (121) is clamped to the adjusting cover (131) to enable a circumferential positioning of the suction nozzle (121) and the adjusting cover (131); the suction nozzle (121) is movable along an axial direction to engage with the adjusting cover (131) or disengage from the adjusting cover (131); an elastic member is arranged between the suction nozzle (121) and the adjusting cover (131) to provide an elasticity for keeping the suction nozzle (121) from disengaging from the adjusting cover (131).

16. An electronic cigarette, comprising an atomizer device, wherein the atomizer device comprises a housing, a liquid reservoir chamber (115) defined in the housing, and an adjusting member (13) engaging with the housing; the adjusting member (13) is arranged on the housing; a liquid injection channel (1131) is defined on the housing for injecting liquid solution into the liquid reservoir chamber (115); the adjusting member (13) is movable between a first position and a second position along the upper surface of the housing and keeps connected to the housing while moving relative to the housing; the adjusting member (13) is able to move to the first position to open the liquid injection channel (1131), and is able to move to the second position to close the liquid injection channel (1131); the atomizer device comprises an air flowing passage (112).

17. The electronic cigarette of claim 16, wherein the atomizer device comprises a cartridge (111) encircled the air flowing passage (112), and the sealing unit (113) is arranged on one end of the cartridge (111) corresponding to the air flowing passage (112); the liquid reservoir chamber (115) is defined between the cartridge (111) and the air flowing passage (112).

18. The electronic cigarette of claim 16, wherein the atomizer device comprises a sealing unit (113) sealing one end of the liquid reservoir chamber (115), the liquid injection channel (1131) is defined on the sealing unit (113); the sealing unit (113) comprises an annular sealing cover (113*a*) correspondingly engaging with the adjusting member (13), and a second opening of the liquid injection channel (1131) is defined in the sealing cover (113*a*); and the adjusting member (13) comprises an adjusting cover (131) movably contacting the sealing cover (113*a*).

19. The electronic cigarette of claim 16, wherein the sealing unit (113) comprises a fastening member (1132) and a sealing plug (1133); the fastening member (1132) comprises a plate (1135), a first sleeving portion (1136) arranged on an inner periphery of the plate (1135), and a second sleeving portion (1137) arranged on an outer periphery of the plate (1135); the first sleeving portion (1136) and the second sleeving portion (1137) engage with an inner wall of the air flowing passage (112) and an outer wall of a cartridge (111) respectively; the sealing plug (1133) seals a gap between an outer wall of the air flowing passage (112) and an inner wall of a cartridge (111), and the plate (1135) is located between the sealing cover (113*a*) and the sealing plug (1133); and a third opening and a fourth opening of the liquid injection channel (1131) are defined in the plate (1135) and the sealing plug (1133) respectively.

20. An atomizer device, comprising a housing, a liquid reservoir chamber (115) defined in the housing, and an adjusting member (13) engaging with the housing; wherein the adjusting member (13) is arranged on the housing; a liquid injection channel (1131) is defined the housing for injecting liquid solution into the liquid reservoir chamber (115); the adjusting valve (13) is rotatable between a first position and a second position along the upper surface of the housing and keeps connected to the housing while rotating relative to the housing; the adjusting member (13) is able to be rotated to the first position to open the liquid injection channel (1131), and is able to be rotated to the second position to close the liquid injection channel (1131); the atomizer device comprises an air flowing passage (112) and an atomizer assembly (15) fluidly connected to the air flowing passage (112).

\* \* \* \* \*